(12) United States Patent
Morello

(10) Patent No.: US 9,974,894 B2
(45) Date of Patent: May 22, 2018

(54) BLOOD PUMP SYSTEM

(75) Inventor: Gino F. Morello, Houston, TX (US)

(73) Assignee: ReliantHeart, Inc., Houston, TX (US)

( * ) Notice: Subject to any disclaimer, the term of this patent is extended or adjusted under 35 U.S.C. 154(b) by 1326 days.

(21) Appl. No.: 12/594,792

(22) PCT Filed: Apr. 7, 2008

(86) PCT No.: PCT/US2008/059585
§ 371 (c)(1),
(2), (4) Date: Jan. 12, 2010

(87) PCT Pub. No.: WO2008/124696
PCT Pub. Date: Oct. 16, 2008

(65) Prior Publication Data
US 2010/0130809 A1    May 27, 2010

Related U.S. Application Data

(60) Provisional application No. 60/910,369, filed on Apr. 5, 2007.

(51) Int. Cl.
*A61M 1/10* (2006.01)
*A61M 1/12* (2006.01)

(52) U.S. Cl.
CPC .......... *A61M 1/1086* (2013.01); *A61M 1/101* (2013.01); *A61M 1/122* (2014.02); *A61M 2205/3331* (2013.01); *A61M 2205/8212* (2013.01)

(58) Field of Classification Search
CPC .... A61M 1/101; A61M 1/122; A61M 1/1086; A61M 2205/3331; A61M 2205/8212

USPC .......................................... 600/17; 604/6.09
See application file for complete search history.

(56) References Cited

U.S. PATENT DOCUMENTS

| 4,718,903 A | 1/1988 | Min et al. |
|---|---|---|
| 4,828,543 A * | 5/1989 | Weiss ...................... A61M 1/16 210/637 |
| 5,147,388 A | 9/1992 | Yamazaki |

(Continued)

FOREIGN PATENT DOCUMENTS

WO    WO2004012806    2/2004

OTHER PUBLICATIONS

International Search Report for International Patent Application No. PCT/US2008/059585.

(Continued)

*Primary Examiner* — Michael Carey
(74) *Attorney, Agent, or Firm* — Jones Walker LLP

(57) ABSTRACT

A blood pump system and methods for the use and operation of such a blood system is described, wherein the blood pump system includes an implantable pump and an implantable flow measurement device. A processing device receives indications of a number of pump parameters such as pump voltage, pump current and pump speed. Flow rate is determined based on the pump parameters, and this determined flow rate is compared to the actual flow rate as measured by the flow measurement device. In certain embodiments, the flow measurement device may be periodically energized to make the comparison, then powered off to reduce power consumption. The time period in which the flow measurement device is powered off is based on the difference between the determined and the actual flow rates.

16 Claims, 5 Drawing Sheets

(56) References Cited

U.S. PATENT DOCUMENTS

| | | | | |
|---|---|---|---|---|
| 5,910,252 | A * | 6/1999 | Truitt | A61M 1/16 210/103 |
| 6,063,034 | A * | 5/2000 | Doten | A61B 8/06 600/448 |
| 6,899,691 | B2 * | 5/2005 | Bainbridge et al. | 604/4.01 |
| 7,004,924 | B1 * | 2/2006 | Brugger | A61M 1/3626 600/16 |
| 7,540,851 | B2 * | 6/2009 | O'Mahony et al. | 604/6.09 |
| 2005/0004502 | A1 * | 1/2005 | O'Mahony | A61M 1/3653 604/4.01 |

OTHER PUBLICATIONS

Written Opinion for International Patent Application No. PCT/US2008/059585.
International Preliminary Report on Patentability for International Patent Application No. PCT/US2008/059585.

\* cited by examiner

BLOOD PUMP SYSTEM

CROSS REFERENCE TO RELATED APPLICATIONS

The present application claims priority to U.S. Provisional Patent Application Ser. No. 60/910,369, filed Apr. 5, 2007, the contents of all of which are incorporated herein by reference.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

This disclosure relates generally to blood pump systems, and more particularly to blood pump systems and operation methods associated therewith.

Description of the Related Art

Generally, blood pump systems are employed in either of two circumstances. First, a blood pump may completely replace a human heart that is not functioning properly, or second, a blood pump may boost blood circulation in patients whose heart is still functioning although pumping at an inadequate rate.

For example, U.S. Pat. No. 6,183,412, which is commonly assigned and incorporated herein by reference in its entirety, discloses a ventricle assist device (VAD) commercially referred to as the "DeBakey VAD®." The VAD® is a miniaturized continuous axial-flow pump designed to provide additional blood flow to patients who suffer from heart disease. The device is attached between the apex of the left ventricle and the aorta.

Many known blood pump systems typically are controlled in an open loop fashion where a predetermined speed is set and the flow rate varies according to the pressure differential across the pump. The pump itself may be controlled in a closed loop fashion, wherein the actual pump speed is fed back to a motor controller that compares the actual speed to the desired predetermined speed and adjusts the pump accordingly. Other pumps may be controlled in a closed loop fashion, in which the pump speed is varied according to a monitored parameter of the patient, such as the patient's pulse or blood flow rate.

Whether the pump is operated in a closed loop or open loop fashion, it is desirable to monitor several pump operating parameters, such as voltage level, current level, pump speed, flow rate, and the like. Adding additional measurement devices to the pump system, however, can complicate the system and add to the power requirements for the system.

BRIEF SUMMARY OF THE INVENTION

The teachings of the present disclosure concern a blood pump system such as a VAD (ventricle assist device) system. The pump system includes, for example, an implantable pump and a controller for controlling the pump. The system further includes an implantable flow measurement device. A processing device receives indications of pump parameters such as pump voltage, pump current and pump speed. Flow rate is determined based on the pump parameters, and this determined flow rate is compared to the actual flow rate as measured by the flow measurement device. The flow measurement device may be periodically energized to make the comparison, then powered off to reduce power consumption. The time period in which the flow measurement device is powered off is based on the difference between the determined and the actual flow rates.

Thus, in accordance with a first aspect of the present disclosure, a blood pump system is described, wherein the blood pump system comprises a pump, a flow measurement device configured to measure the flow rate of fluid being pumped, and a processing device receiving indications of pump parameters, the processing device being programmed to determine flow rate based on the pump parameters and compare the determined flow rate to the measured flow rate. In further accordance with this aspect of the disclosure, the determined flow rate may be periodically compared to the measured flow rate, and the flow measurement device may periodically be powered off. Additionally, in the event of the flow measurement device periodically powering off, the device is powered off for a period of time that is determined in response to the difference between the flow rate and the measured flow rate. In further accordance with the first aspect of the disclosure, the pump parameters may be selected from a group comprising pump voltage, pump current, and pump speed, as well as combinations of such parameters, and the processor accesses a look-up table or uses a polynomial modeling or similar such system to determine the flow rate, although the processor may directly calculate the flow rate based on the pump parameters.

In accordance with a second aspect of the present disclosure, a method of operating a blood pump system is described, wherein the method comprises sampling parameters of a blood pump, measuring the flow rate of fluid being pumped, determining flow rate based on the pump parameters, and comparing the determined flow rate to the measured flow rate. In further accordance with this aspect of the disclosure, the determined flow rate may be periodically compared to the measured flow rate, and the flow measurement device may periodically be powered off. Additionally, in the event of the flow measurement device periodically powering off, the device is powered off for a period of time that is determined in response to the difference between the flow rate and the measured flow rate. In further accordance with the first aspect of the disclosure, the pump parameters may be selected from a group comprising pump voltage, pump current, and pump speed, as well as combinations of such parameters, and the processor accesses a look-up table or uses a polynomial modeling or similar such system to determine the flow rate, although the processor may directly calculate the flow rate based on the pump parameters.

BRIEF DESCRIPTION OF THE SEVERAL VIEWS OF THE DRAWINGS

The following figures form part of the present specification and are included to further demonstrate certain aspects of the present invention. The invention may be better understood by reference to one or more of these figures in combination with the detailed description of specific embodiments presented herein.

Figure 1:
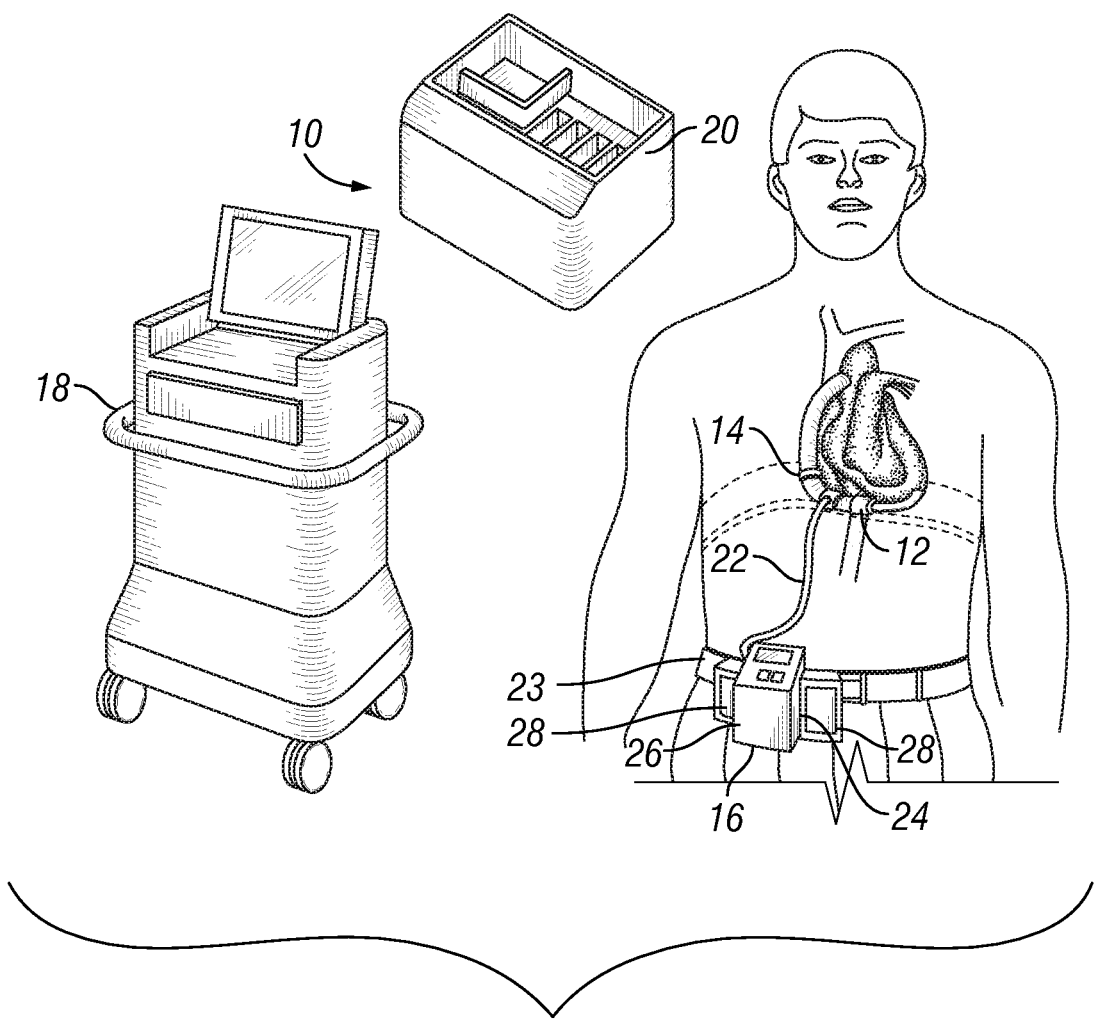
FIG. 1 schematically illustrates various components of an implantable pump system in accordance with teachings of the present disclosure.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Particular embodiments of the invention may be described below with reference to block diagrams and/or operational illustrations of methods.

It will be understood that each block of the block diagrams and/or operational illustrations, and combinations of blocks in the block diagrams and/or operational illustrations, can be implemented by analog and/or digital hardware, and/or computer program instructions. Such computer program instructions may be provided to a processor of a general-purpose computer, special purpose computer, ASIC, and/or other programmable data processing system. The executed instructions may create structures and functions for implementing the actions specified in the block diagrams and/or operational illustrations. In some alternate implementations, the functions/actions/structures noted in the figures may occur out of the order noted in the block diagrams and/or operational illustrations. For example, two operations shown as occurring in succession, in fact, may be executed substantially concurrently or the operations may be executed in the reverse order, depending upon the functionality/acts/structure involved.

Computer programs for use with or by the embodiments disclosed herein may be written in an object oriented programming language, conventional procedural programming language, or lower-level code, such as assembly language and/or microcode. The program may be executed entirely on a single processor and/or across multiple processors, as a stand-alone software package or as part of another software package.

In general terms, Applicants have created a blood pump system and method of operating such a blood pump system, wherein the system can be programmed to determine flow rates based on pump parameters and the measured flow rate, wherein the power usage of the device may be controlled using such determined flow rates.

Turning to the figures, FIG. 1 illustrates an exemplary blood pump system in accordance with the teachings of this disclosure. The illustrated system is a ventricular assist device (VAD) system 10 such as disclosed in U.S. Pat. No. 6,183,412, which is commonly assigned and incorporated herein by reference in its entirety. The VAD system 10 includes components designed for implantation within a human body and components external to the body. Implantable components include a rotary pump 12 and a flow sensor 14. The external components include a portable controller module 16, a clinical data acquisition system (CDAS) 18, and a patient home support system (PHSS) 20. The implanted components are connected to the controller module 16 via a percutaneous cable 22.

Figure 2:
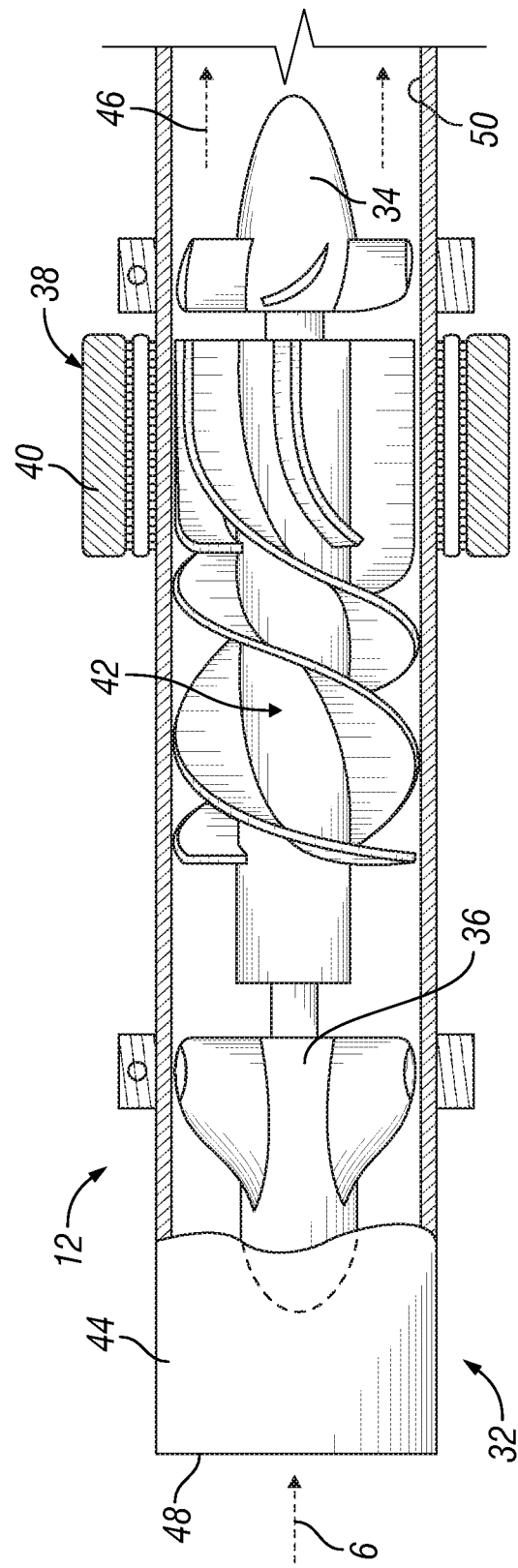
FIG. 2 illustrates a cross-sectional view of an exemplary implantable pump in accordance with teachings of the present disclosure.

The VAD System 10 may incorporate an implantable continuous-flow blood pump, such as the various embodiments of axial flow pumps disclosed in U.S. Pat. Nos. 5,527,159 or in 5,947,892, both of which are incorporated herein by reference in their entirety. An example of a blood pump suitable for use in an embodiment of the invention is illustrated in FIG. 2. The exemplary pump 12 includes a pump housing 32, a diffuser 34, a flow straightener 36, and a brushless DC motor 38, which includes a stator 40 and a rotor 42. The housing 32 includes a flow tube 44 having a blood flow path 46 therethrough, a blood inlet 48, and a blood outlet 50.

The stator 40 is attached to the pump housing 32, is preferably located outside the flow tube 44, and has a stator field winding 52 for producing a stator magnetic field. In one embodiment, the stator 40 includes three stator windings and may be three phase "Y" or "Delta" wound. The rotor 42 is located within the flow tube 44 for rotation in response to the stator magnetic field, and includes an inducer 58 and an impeller 60. Excitation current is applied to the stator windings 52 to generate a rotating magnetic field. A plurality of magnets 62 are coupled to the rotor 42. The magnets 62, and thus the rotor 42, follow the rotating magnetic field to produce rotary motion.

Figure 3:
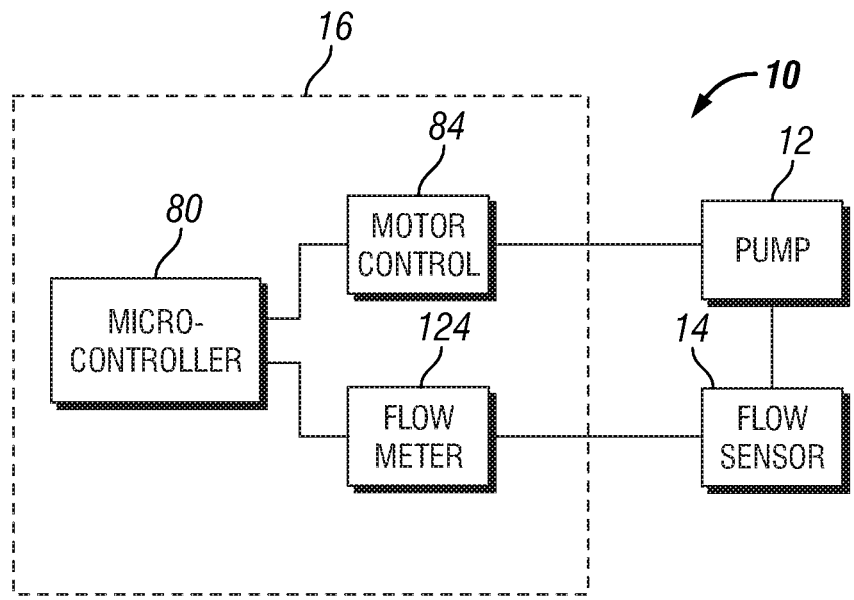
FIG. 3 illustrates a block diagram illustrating aspects of a controller module in accordance with teachings of the present disclosure.

FIG. 3 conceptually illustrates additional aspects of the exemplary pump system 10. More specifically, portions of the controller module 16 and the pump 12 are shown. The controller module 16 includes a processor, such as a microcontroller 80, which in one embodiment of the invention is a model PIC16C77 microcontroller manufactured by Microchip Technology, Inc. (Chandler, Ariz.). The microcontroller 80 includes a multiple channel analog to digital (A/D) converter, which receives indications of motor parameters from the motor controller 84. Thus, the controller module 16 may monitor parameters such as instantaneous motor current, the AC component of the motor current, and motor speed.

In exemplary embodiments of the invention, the motor controller 84 comprises a Micro Linear ML4425 Motor Controller (available from Micro Linear corporation, San Jose, Calif.). The operation of the brushless DC motor 38 of the present invention requires that current be applied in a proper sequence to the stator windings 52 to create the rotating field. Two stator windings 52 have current applied to them at any one time, and by sequencing the current on and off to the respective stator windings 52, the rotating magnetic field is produced. In an embodiment of the invention, the motor controller 84 senses back electromotive force (EMF) voltage from the motor windings 52 to determine the proper commutation phase sequence using phase lock loop (PLL) techniques. Whenever a conductor, such as a stator winding 52, is "cut" by moving magnetic lines of force, such as are generated by the magnets 62 of the brushless DC motor 38, a voltage is induced. The voltage will increase with rotor speed 42. It is possible to sense this voltage in one of the three stator windings 52 because only two of the motor's windings 52 are activated at any one time, to determine the rotor 42 position.

An alternative method of detecting the rotor 42 position relative to the stator 40 for providing the proper stator winding 52 excitation current sequence is to use a position sensor, such as a Hall effect sensor or a fluxgate sensor. Implementing aspects of the present invention using a motor with rotor position sensors, rather than a sensorless motor, would be a routine undertaking for one skilled in the art having the benefit of this disclosure. However, adding additional components, such as Hall effect sensors, requires additional space, which is limited in any implanted device application. Further, using a position detection device adds sources of system failures.

The actual pump speed is determined and fed back to the controller module 16, which compares the actual speed to a desired predetermined speed and adjusts the pump 12 accordingly. In accordance with certain embodiments of the invention, the pump 12 may be controlled in a closed loop fashion wherein the desired pump speed is varied for events such as sleeping, normal activity or high energy exertion.

The embodiment shown in FIG. 3 further includes an integral flow meter 124. At least one flow sensor 14 is implanted down stream of the pump 12. Alternately, a flow sensor 14 may be integrated with the pump 12. The flow meter 124 is coupled between the implanted flow sensor 14 and the microcontroller 80. The flow meter 124 receives data from the flow sensor 14 and outputs flow rate data to the microcontroller 80, allowing the system to monitor instantaneous flow rate.

The flow sensor 14 and flow meter 124 may be employed to continuously measure real-time blood flow rate, providing a true, calibrated, and independent metric of blood flow while consuming approximately 0.5 Watts. Power reductions, however, may be obtained by deriving flow directly from intrinsic pump signals. The algorithmic approach to deriving blood flow rate described herein may function autonomously or in conjunction with the existing real-time flow meter 124.

Figure 4:
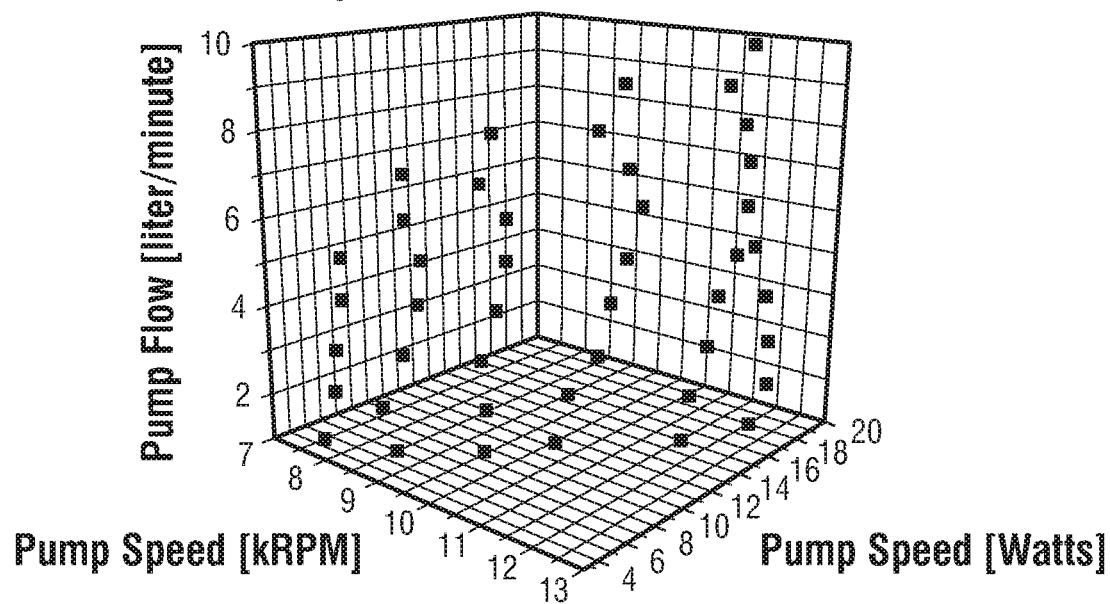
FIG. 4 illustrates a multi-dimensional data table correlating pump flow, pump speed, and pump power.

A primary data table containing flow versus power and speed information is stored as a multidimensional matrix into the memory of the microcontroller 80. FIG. 4 shows an example of such a data table. The microcontroller 80 is then programmed to sample the pump's analog voltage, current and speed signals and, via a lookup into the primary data table, outputs the corresponding flow value for display and pump control purposes.

The real-time flow meter 124 is periodically energized and its output compared to the derived value. The duty cycle used to control the real-time flow meter 124 is proportional to the difference between the actual measured flow and derived flow values the more closely they match the less often the flow meter 124 is energized. Additionally, a secondary data table containing actual flow, derived flow, voltage, current, and speed information is stored and used to prove that the algorithm performs correctly over the course of its use. A compilation of secondary data tables from multiple patients may also be used to further optimize the primary data table. While this particular aspect illustrates the use of look-up tables by the processor to determine flow rate, other appropriate measurements may be used, such as polynomial modeling systems and other know, suitable alternatives to look-up tables.

The application of this duty cycle control of the real-time flow meter 124 along with a flow estimation algorithm yields a system which can continually and reliably output accurate flow information while consuming less than one-tenth ($\frac{1}{10}$) the power of the flow meter 124 itself. This hybrid approach further allows the algorithm to be tested in a safe and controlled manner and reduces power consumption by more than a magnitude while maintaining the precision of the existing real-time flow meter 124.

Figure 5:
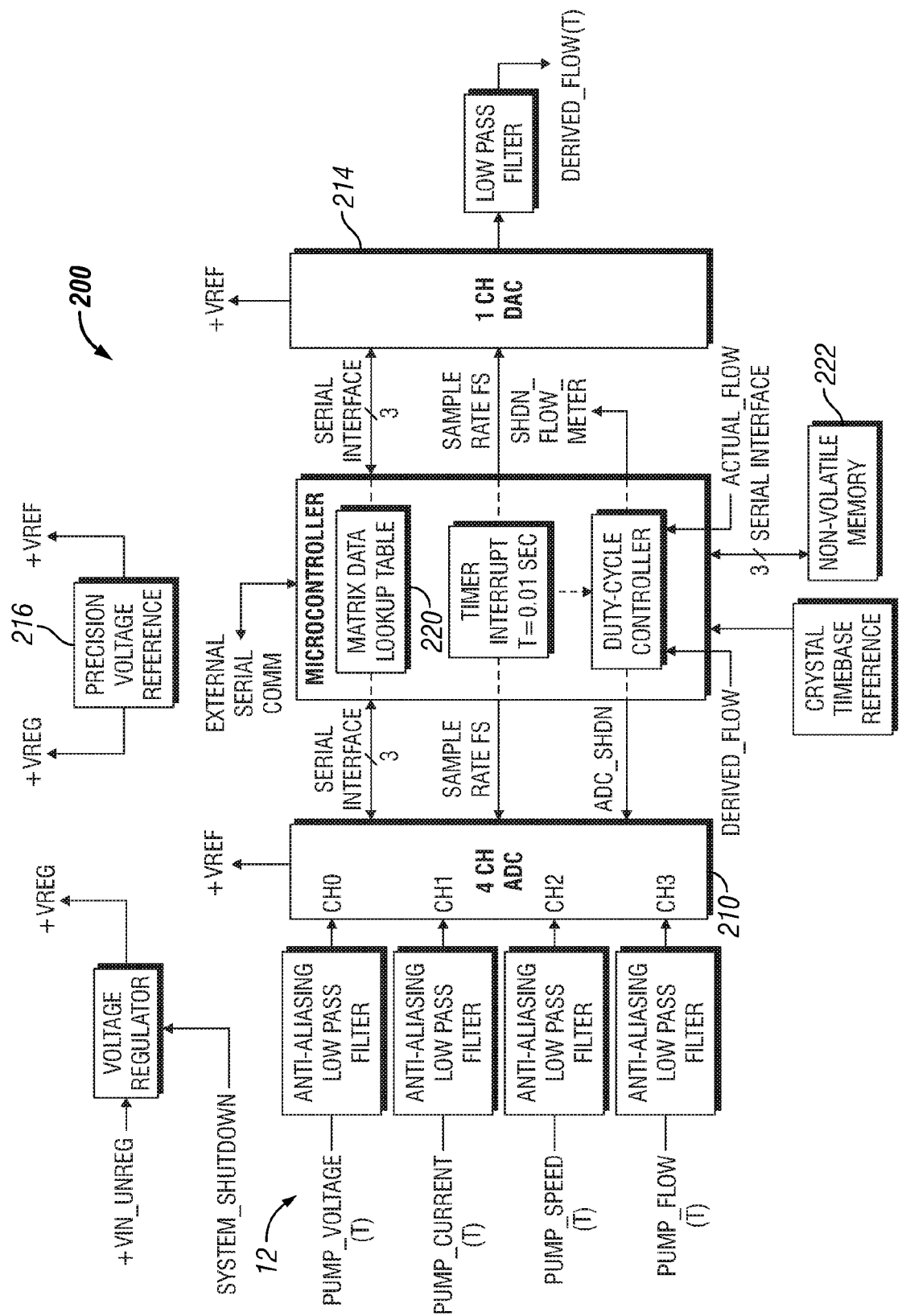
FIG. 5 illustrates a block diagram conceptually illustrating a flow rate determination system in accordance with teachings of the present disclosure.

FIG. 5 is a block diagram conceptually illustrating the flow rate determination system 200, using the pump's intrinsic voltage, current, and speed signals together with the flow meter 124. The system 200 includes a multi-channel analog-to-digital converter (ADC) 210 to sample the intrinsic pump signals 212, a single-channel digital-to-analog converter (DAC) 214 to output derived flow values as a voltage proportional flow, a precision voltage reference (VREF) 216 for use by both the ADC 210 and DAC 214, and the microcontroller 80 to coordinate necessary data acquisition, timing, and discrete digital I/O (input/output) activities. The microcontroller's 80 functionality may be implemented using a low-power Programmable Read Only Memory (PROM), Field Programmable Gate Array (FPGA), Complex Programmable Logic Device (CPLD), or other suitable device.

Pump power is the product of pump voltage and current. Therefore, the multi-dimensional matrix may be reduced in complexity by one dimension if the system first derives pump power by calculating the product of the sampled pump voltage and current signals. As discussed above, a derived flow value is extracted from a primary data table 220 containing a multidimensional matrix filled with pump flow versus pump voltage, pump current, and pump speed data values, such as the table illustrated in FIG. 4. The sampled values function as pointers into the table. In exemplary systems, the multi-dimensional matrix is filled with linearly (evenly) distributed pump flow versus pump voltage, pump current, and pump speed data values. In other implementations, the multi-dimensional matrix is filled with non-linearly (non-evenly) distributed pump flow versus pump voltage, pump current, and pump speed data values to provide higher resolution and accuracy in areas where there may exist large changes in flow with respect to voltage, current, and/or speed. The system may interpolate the data in areas between programmed data points. Further, the type of interpolation used may be selected as a function of where on the pump's characteristic curves the system is operating.

Alternatively, the derived flow value may be calculated directly using the equation that determines the derived flow as a function of pump power and speed:

derived_flow=f(pump_power,pump_speed).

This method potentially provides greater accuracy with greater computational complexity and with greater power consumption. More specifically, benefits include increased system reliability, decreased component count, decreased power consumption, decreased heat dissipation, decreased conductor count (girth) within the percutaneous tether, decreased VAD interface connector size, decreased cost, decreased controller size/volume, and decreased amount of hardware implanted into patient.

For example, one method of directly deriving flow uses three equations to derive flow rate information from the pump motor's operating characteristics. The equations described below are based on several multiple regression analyses performed on empirical pump motor data (i.e. characteristic curves) detailing various flow rates versus pump motor speed, power (the product of voltage and current), and differential pressure.

Non-linearities within the characteristic performance curves of an exemplary pump system motor suggest that blood flow rate is not a direct function of pump motor speed, motor voltage, and motor current. As such, there may exist multiple flow rates for a given speed and power (product of motor voltage and current). There are, however, unique flow rates for corresponding pump motor speeds, powers, and differential pressures. The pump system measures motor voltage, motor current, and motor speed but not the differential pressure across the pump. Unfortunately, this is not a parameter that is easily measured and would require additional electronic circuitry, software, and pressure transducers to be mounted on the inlet and outlet sides of the VAD pump motor. These pressure transducers and their related hardware and software would increase the complexity of the overall system.

Therefore, it becomes necessary to first calculate differential pressure from motor voltage, current, and speed. The calculated values for differential pressure can then be recombined with motor voltage, current, and speed to calculate unique values of flow rate. This mathematical derivation contains three equations including:

Calculation of Motor Power as a Function of Voltage and Current:

Power(t)=f(Voltage(t), Current(t))

Calculation of Differential Pressure as a function of Power and Speed:

DifferentialPressure(t)=f(Power(t), Speed(t))

Calculation of Flow Rate as a function of Power, Speed, and Differential Pressure:

Flow(t)=f(Power(t), Speed(t), DifferentialPressure(t)

Figure 6:
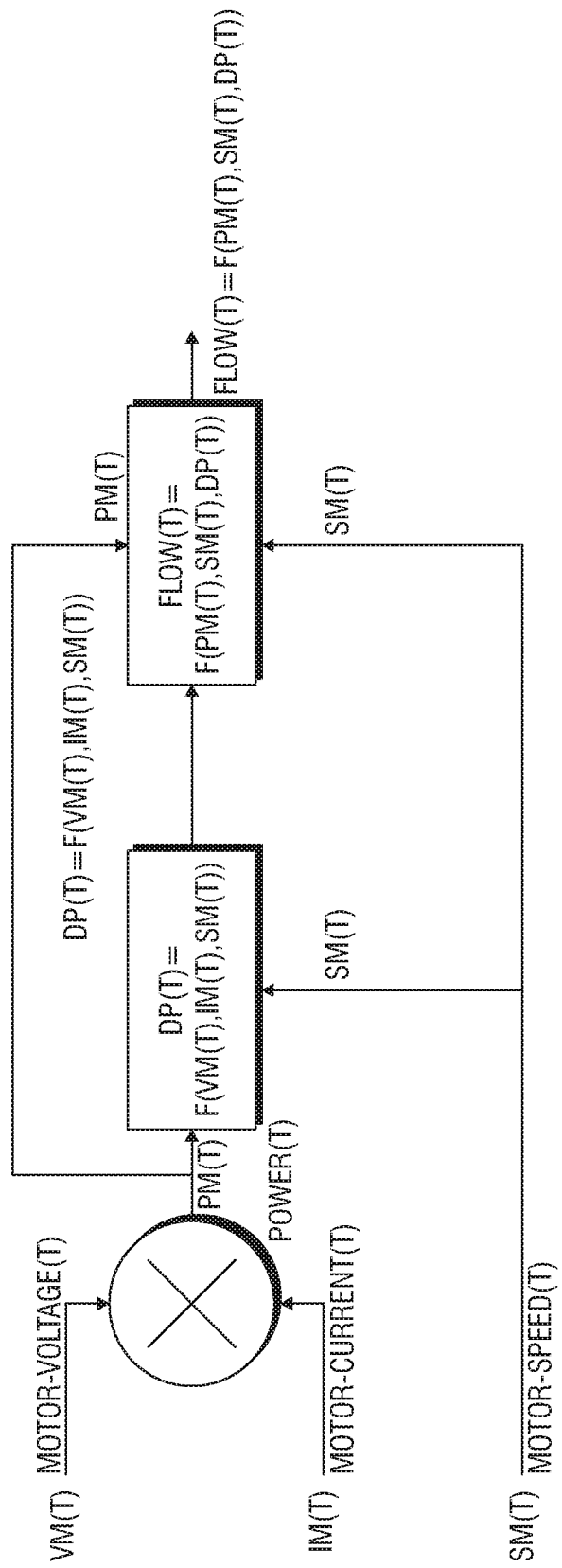
FIG. 6 illustrates a block diagram showing a flow calculation process in accordance with teachings of the present disclosure.

FIG. 6 is a block diagram illustrating the flow calculation process. The system must first sample motor voltage, motor current, and motor speed. It then must multiply motor voltage and motor current to calculate instantaneous motor power. Pump motor speed is then combined with the calculated instantaneous motor power to calculate differential pressure using the equation for DP(t) (two independent variables; power and speed). Calculated values for differential pressure and corresponding values of motor voltage, motor current, and motor speed are then combined to calculate flow rate using the equation for Flow(t) (three independent variables; power, speed, and differential pressure).

The equations for Power and Differential Pressure may be substituted for their respective independent variables in the equation for Flow. This will ultimately yield a single equation for Flow as a function of Power and Speed. In an exemplary implementation, the equations for Flow(t) and DP(t) were developed through the application of multiple regression techniques performed on empirical in-vitro pump performance data. Approximately five hundred (500) invitro data points were taken using a MicroMed Flow Loop (MicroMed Technologies, Inc., Houston, Tex.) and related electronic test equipment. Pump Motor voltage, current, inlet/outlet differential pressure, and flow rate were measured and logged. The data was taken between one thousand (1000) RPM and twelve thousand five hundred (12,500) RPM in five hundred (500) RPM graduations. The equation for Flow(t) is based on the use of three independent variables (power, speed, and differential pressure) and the equation for DP(t) is based on the use of two independent variables (power and speed).

The equation for Flow(t) was developed by first generating a simple regression equation (y=a+b*X1+c*X2+d*X3), evaluating its correlation matrix, and then further refining the equation. This was repeated such that better fits were achieved. Approximately fifty equations were generated and evaluated with the best fit having a coefficient of multiple determination of $R^2$=0.9910 and an adjusted coefficient of multiple determination of $R_a^2$=0.9903. This "best fit" equation is highly deterministic explaining over 99.1% of the variation within the data set.

A second regression analysis detailing the development of the equation for DP(t) was also performed in the same iterative fashion. Approximately four hundred equations were generated and evaluated with the best fit equation having a coefficient of multiple determination of $R^2$=0.9334 and an adjusted coefficient of multiple determination of $R_a^2$=0.9303. This "best fit" equation is also highly deterministic explaining 93.0% of the variation within the data set.

The accuracy of the equation for Power is 100% ($R^2$=1.000) because it is simply the product of motor voltage and current. The accuracy of the entire model is the product of each equation's multiple coefficient of determination with $R_{power}^2$=1.000, $R_{Flow}^2$=0.9910, and $R_{DP}^2$=0.9334. The result is $R_{Total}^2$=0.9250 and therefore the entire model accounts for 92.5% of the variation within the data set.

A third regression analysis was performed to further justify the need for using the intermediate DP(t) calculation. This third regression analysis details the development of an equation for Flow as a function of Power and Speed. Approximately four hundred equations were generated and evaluated with the best fit equation having a coefficient of multiple determination of $R^2$=0.8244 and an adjusted coefficient of multiple determination of $R_a^2$=0.8162. The accuracy of the entire model is the product of each equation's multiple coefficient of determination with $R_{power}^2$=1.000 and $R_{Flow}^2$=0.8244. The result is $R_{Total}^2$=0.8244 and therefore the entire model accounts for 82.44% of the variation within the data set, ten (10) percent less accurate than the model which utilizes the intermediate DP(t) calculation.

The mathematical derivation may be implemented in software and/or hardware. Software implementations include using the existing microcontroller 84, an additional stand-alone microcontroller, a Digital Signal Processor (DSP). Hardware implementations may include a Field Programmable Gate Array (FPGA), Complex Programmable Logic Device (CPLD) or Application Specific Integrated Circuit (ASIC), for example.

As noted above, the derived flow value is periodically compared to the actual flow value as measured with the dedicated real-time flow meter 124 and sensor 14, and the difference between the actual and calculated flow rate values is used as the basis for duty-cycle control of a dedicated real-time flow probe and flow meter. Small differences between the actual and derived flow values will allow the real-time flow meter to remain unpowered for longer periods of time saving valuable system power and, conversely, large differences will force the real-time flow meter to be powered on more often. Moreover, the magnitude of the difference between the actual and derived flow values may be used to indicate that a flow restriction, abnormality, or perturbation exists in the flow path to or from the pump.

The exemplary system 200 shown in FIG. 5 also contains additional programmable non-volatile memory (e.g. EEPROM, FLASH, etc.) used to store a secondary multi-dimensional data matrix 222. This memory is used to acquire in real-time actual pump flow, derived flow, pump speed, and pump power data for archival and post-processing purposes. The secondary multidimensional data matrix 222 may further be used for future refinement and optimization of the primary multi-dimensional matrix or directly implemented derived flow equation.

In still further implementations, the actual pump power is compared to derived pump power. The actual pump power is the product of pump voltage and pump current and the derived pump power is obtained based on the pump flow and speed. The derived power value may be extracted from a primary data table containing a multi-dimensional matrix filled with pump flow versus pump speed data values, wherein the sampled values of flow and speed function as pointers into the table. This multi-dimensional matrix may be filled with linearly (evenly) distributed pump flow versus pump speed data values, or with non-linearly (non-evenly) distributed pump flow versus speed data values to provide higher resolution and accuracy in areas where there may exist large changes in power with respect to flow and/or speed. The system interpolates the data in areas between programmed data points, and the type of interpolation used may be selected as a function of where on the pump's characteristic curves the system is operating.

The derived power value may be periodically compared to the actual power value, and the difference between the actual and calculated power values is used as the basis for duty-cycle control of the dedicated real-time flow sensor 14 and flow meter 124. Small differences between the actual and derived power values will allow the real-time flow meter 124 to remain unpowered for longer periods of time saving valuable system power and, conversely, large differences will force the real-time flow meter 124 to be powered on more often. Still further, the magnitude of the difference between the actual and derived power values may be used to indicate that a flow restriction, abnormality, or perturbation exists in the flow path to or from the pump.

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intends to protect all such modifications and improvements to the full extent that such falls within the scope or range of equivalent of the following claims.

What is claimed is:

1. A blood pump system comprising:
a pump;
a flow measurement device configured to measure the flow rate of fluid being pumped; and
a processing device receiving indications of pump parameters, the processing device being programmed to—
determine flow rate based on the pump parameters,
power the flow measurement device on according to a duty cycle,
extract a measured flow rate from the flow measurement, when the flow measurement device is powered on,
power the flow measurement device off according to the duty cycle,
compare the determined flow rate to the measured flow rate,
adjust the duty cycle proportionally to a difference between the determined flow rate and the measured flow rate, and
control the pump based at least in part on the determined flow rate when the flow measurement device is powered off.

2. The blood pump system of claim 1, wherein the difference between the determined flow rate and the measured flow rate is used it indicate an abnormality in a flow path of the pump.

3. The blood pump system of claim 1, wherein the processor is further programmed to optimize its determination of the determined flow rate based on the difference between the determined flow rate and the measured flow rate.

4. The blood pump system of claim 1, wherein the processing device accesses a look-up table to determine the flow rate.

5. The blood pump system of claim 1, wherein the processing device uses polynomial modeling to determine the flow rate.

6. The blood pump system of claim 1, wherein the processing device determines the flow rate by directly calculating the flow rate based on the pump parameters.

7. A blood pump system comprising:
a pump;
a flow measurement device configured to measure the flow rate of fluid being pumped; and
a processing device receiving indications of pump parameters, the processing device being programmed to—
determine a determined flow rate based on the pump parameters,
power the flow measurement device on,
extract a measured flow rate from the flow measurement device, when the flow measurement device is powered on,
power the flow measurement device off,
compare the determined flow rate to the measured flow rate, optimize the determination of the determined flow rate based on the difference between the determined flow rate and the measured flow rate, and control the pump based on the determined flow rate when the flow measurement device is powered off.

8. The blood pump system of claim 7, wherein the difference between the determined flow rate and the measured flow rate is used it indicate an abnormality in a flow path of the pump.

9. The blood pump system of claim 7, wherein the processing device accesses a look-up table to determine the flow rate.

10. The blood pump system of claim 7, wherein the processing device uses polynomial modeling to determine the flow rate.

11. The blood pump system of claim 7, wherein the processing device determines the flow rate by directly calculating the flow rate based on the pump parameters.

12. A blood pump system comprising:
a pump;
a flow measurement device configured to measure the flow rate of fluid being pumped; and
a processing device receiving indications of pump parameters, the processing device being programmed to—
determine a determined flow rate by accessing a primary data table using the pump parameters,
power the flow measurement device on,
extract a measured flow rate from the flow measurement device, when the flow measurement device is powered on,
power the flow measurement device off,
compare the determined flow rate to the measured flow rate, and
populate a secondary data table with corresponding pump parameters, determined flow rate, and measured flow rate, and
optimize the primary data table based on the secondary data table.

13. The blood pump system of claim 12, wherein the difference between the determined flow rate and the measured flow rate is used it indicate an abnormality in a flow path of the pump.

14. The blood pump system of claim 12, wherein the processing device accesses a look-up table to determine the flow rate.

15. The blood pump system of claim 12, wherein the processing device uses polynomial modeling to determine the flow rate.

16. The blood pump system of claim 12, wherein the processing device determines the flow rate by directly calculating the flow rate based on the pump parameters.

* * * * *